(12) United States Patent
Goldfine et al.

(10) Patent No.: US 7,188,532 B2
(45) Date of Patent: Mar. 13, 2007

(54) SELF-MONITORING METALS, ALLOYS AND MATERIALS

(75) Inventors: Neil J. Goldfine, Newton, MA (US); Vladimir A. Zilberstein, Chestnut Hill, MA (US); David C. Grundy, Reading, MA (US); Andrew P. Washabaugh, Chula Vista, CA (US); Darrell E. Schlicker, Watertown, MA (US); Ian C. Shay, Waltham, MA (US); Robert J. Lyons, Boston, MA (US); Christopher A. Craven, Bedford, MA (US); Christopher Root, Boulder, CO (US); Mark D. Windoloski, Burlington, MA (US); Volker Weiss, Syracuse, NY (US)

(73) Assignee: Jentek Sensors, Inc., Waltham, MA (US)

( * ) Notice: Subject to any disclaimer, the term of this patent is extended or adjusted under 35 U.S.C. 154(b) by 0 days.

(21) Appl. No.: 10/937,105

(22) Filed: Sep. 8, 2004

(65) Prior Publication Data

US 2005/0083032 A1    Apr. 21, 2005

Related U.S. Application Data

(60) Provisional application No. 60/591,662, filed on Jul. 27, 2004, provisional application No. 60/573,026, filed on May 19, 2004, provisional application No. 60/569,216, filed on May 7, 2004, provisional application No. 60/526,168, filed on Dec. 2, 2003, provisional application No. 60/520,000, filed on Nov. 14, 2003, provisional application No. 60/505,197, filed on Sep. 23, 2003, provisional application No. 60/501,504, filed on Sep. 8, 2003.

(51) Int. Cl.
*G01B 7/16* (2006.01)
(52) U.S. Cl. .................................................. 73/779
(58) Field of Classification Search .................. 73/779
See application file for complete search history.

(56) References Cited

U.S. PATENT DOCUMENTS 4,814,690 A    3/1989    Melcher et al.

(Continued)

FOREIGN PATENT DOCUMENTS

| EP | 0 666 470 A2 | 8/1995 |
|---|---|---|
| JP | 2001281225 | 10/2001 |

OTHER PUBLICATIONS

Bozorth, R.M., Ferromagnetism, IEEE Press, 1978.

(Continued)

*Primary Examiner*—Max Noori
(74) *Attorney, Agent, or Firm*—Hamilton, Brook, Smith & Reynolds, P.C.

(57) ABSTRACT

Observability of damage precursor, damage and usage states, or event occurrence may be enhanced by modifying component materials to include self-monitoring materials or by processing test material to alter the surface properties. The properties of the self monitoring materials, such as magnetic permeability or electrical conductivity, are monitored with electromagnetic sensors and provide greater property variations with component condition than the original component material. Processing includes shot peening or laser welding.

13 Claims, 12 Drawing Sheets

U.S. PATENT DOCUMENTS

| | | | |
|---|---|---|---|
| 4,944,185 | A | 7/1990 | Clark, Jr. et al. |
| 5,015,951 | A | 5/1991 | Melcher |
| 5,453,291 | A | 9/1995 | Sasahara et al. |
| 5,453,689 | A | 9/1995 | Goldfine et al. |
| 5,615,466 | A | 4/1997 | Safari et al. |
| 5,793,206 | A | 8/1998 | Goldfine et al. |
| RE36,986 | E | 12/2000 | Melcher |
| 6,188,218 | B1 | 2/2001 | Goldfine et al. |
| 6,380,747 | B1 | 4/2002 | Goldfine et al. |
| 6,486,673 | B1 | 11/2002 | Goldfine et al. |
| 6,657,429 | B1 | 12/2003 | Goldfine et al. |
| 2002/0075006 | A1 | 6/2002 | Goldfine et al. |
| 2002/0158626 | A1 | 10/2002 | Shay et al. |
| 2002/0163333 | A1 | 11/2002 | Schlicker et al. |
| 2003/0071615 | A1 | 4/2003 | Schlicker et al. |
| 2003/0080744 | A1 | 5/2003 | Goldfine et al. |
| 2003/0139763 | A1 | 7/2003 | Chamberlain et al. |
| 2003/0173958 | A1 | 9/2003 | Goldfine et al. |
| 2004/0056654 | A1 | 3/2004 | Goldfine et al. |
| 2004/0225474 | A1 | 11/2004 | Goldfine et al. |
| 2005/0051327 | A1* | 3/2005 | Vinegar et al. ............ 166/256 |

OTHER PUBLICATIONS

NASA Phase I Proposal, titled "Propulsion System Life Management Through Enhanced Observability," Topic #A1.02, dated Sep. 8, 2003.

Army Phase I Proposal, titled "MWM-Array Sensor Networks for Fatigue Monitoring of Army Aircraft," Topic #A03-071, dated Aug. 12, 2003.

Technical presentation titled "landing Gear Inspection Opportunities Using Scanning and Permanently Mounted Eddy Current Sensor Arrays," ATA Conference 2003, Sep. 25, 2003.

Technical presentation titled "MWM Eddy-Current Sensor Arrays for Residual Stress Mapping," ASTM Symposium, Salt Lake City, Utah, May 19-20, 2004.

Technical presentation titled "High-Resolution Residual Stress Imaging Using MWM-Arrays with Pre-Computed Response Databases," QNDE Conference, Colorado School of Mines, Jul. 2004.

* cited by examiner

SELF-MONITORING METALS, ALLOYS AND MATERIALS

RELATED APPLICATIONS

This application claims the benefit of U.S. Provisional Application Nos. 60/501,054 filed Sep. 8, 2003, 60/505,197 filed Sep. 23, 2003, 60/520,000 filed Nov. 14, 2003, 60/526,168 filed Dec. 2, 2003, 60/569,216 filed May 7, 2004, 60/573,026 filed May 19, 2004, and 60/591,662 filed Jul. 27, 2004. The entire teachings of the above applications are incorporated herein by reference.

BACKGROUND OF THE INVENTION

This application addresses nondestructive materials characterization, particularly quantitative, model-based characterization of surface, near-surface, and bulk material condition for flat and curved parts or components using magnetic field based or eddy-current sensors or electric field based capacitive sensors. Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks, cracks or stress variations in magnitude, orientation or distribution.

Conventional eddy-current sensing involves the excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

A typical application of these techniques is the inspection of high-strength steel components with the goal of measuring applied and residual stresses and detecting early stage fatigue damage. Highly stressed aircraft components, such as landing gear components, require the use of steels such as 4340M and 300M heat treated to very high strength levels. The integrity of these components is critical to the safe operation of aircraft and for maintaining readiness of military aircraft. However, unintentional loading of these components, such as a hard landing or during towing or taxiing, can impart residual stresses that compromise the integrity of the component.

Existing magnetic/electromagnetic, diffraction, ultrasonic and other methods for assessment of residual stresses in steel components or monitoring of applied stress over wide areas are not yet practical or cost-effective. Typically, discrete strain gages are mounted directly onto the material under test (MUT). However this requires intimate fixed contact between the strain gage and the MUT and individual connections to each of the strain gages, both of which limit the potential usefulness for monitoring stress over large areas. Furthermore, strain gages are limited in durability and do not always provide sufficient warning of gage failure or malfunction.

Correlations between magnetic properties and stresses in ferromagnetic materials have been studied for over 100 years, as reviewed by Bozorth. Magnetostriction effect data suggests that, depending on the magnitude and sign of the magnetostriction coefficient, correlation between stress and magnetic permeability within certain ranges of the magnetic field should be present. However, attempts to use conventional inductive, i.e., eddy-current sensors for assessment of residual stresses as well as for a number of other applications have shown serious limitations, particularly for complex geometry components. This is typical of many inspections where direct inspections of the component material may only provide limited observability of the property of interest.

SUMMARY OF THE INVENTION

Aspects of the methods described herein involve nondestructive condition monitoring of materials. These conditions include damage, damage precursor and usage states, as well as the occurrence of events. These methods can improve the efficacy of nondestructive examinations and the decisions based on these examinations by providing better assessments of the material state and/or quality.

In one embodiment of the invention, material modifications are made that enhance the observability of a condition state for an article or component. The component base material is modified by a condition sensitive second material so that the combined material construct has a larger electrical property variation with the component condition than is experience by the base material itself. This modification accounts for the measurement capabilities of the inspecting sensor and does not compromise the mechanical or electrical integrity of the component. In one embodiment of the invention, the article itself or a portion of the article as replaced with the condition sensitive material. In another embodiment of the invention, the second material is added to the base material, by a doping or mixing method, preferably in trace amounts, to provide the desired enhance sensitivity to the condition variations. In yet another embodiment, a third material is added, where the ensuing electrical property variation may have sensitivity to the same or different article conditions. In various embodiments of the invention, the condition is stress, temperature, overload, or accumulated fatigue damage. In another embodiment of the invention, processing of the surface of an article enhances the observability of an article condition state. In alternative embodiments of the invention, this processing can be shot peening or laser welding. The article can be a fastener or fitting used on an aircraft.

In various alternative embodiments of the invention, the material condition is monitored with magnetic field based eddy current sensors or sensor arrays. These sensor or sensor arrays can be mounted to the surface or scanned over the surface to examine relatively wide areas. In another embodiment of the invention, for insulating or semi-insulating materials, electric field based dielectric sensors can be used. In other alternative embodiments of the invention, the material property being monitored is an electrical property, which can be the electrical conductivity, magnetic permeability, dielectric permittivity, or variations on these properties. When the electrical property is the magnetic permeability or susceptibility, sensors incorporating permanent magnets may be used. Furthermore, when the electrical property is a magnetic permeability, the Curie temperature of the modified material may be greater than the typical exposure temperature so that the condition of the article can be monitored even at elevated temperatures.

In another embodiment of the invention, landing gear or a landing gear component is monitored during towing operations with one or sensors at locations that provides a directional measure of the applied load. This can be done by measuring an electrical property of the landing gear material and correlating this electrical property measurement with loads applied from calibration measurements. This permits an inspection of the landing gear for damage each time the aircraft is towed and can prevent damage from occurring during taxiing or towing operations that apply excessive or over loads to the landing gear. In one embodiment of the invention, at least one other sensor is also used, which is oriented to be insensitive to typical applied loads, to provide an indication of any atypical loads or residual stress changes in the material. The sensors can be mounted onto or embedded directly into the landing gear materials, or they can be held within a fixture that is connected up to the landing gear during the towing procedure. In one embodiment of the invention, the loads are monitored during the towing procedure and the procedure is altered, if necessary, to ensure that the loads are within an acceptable range. This adjustment can also be done automatically. In yet another embodiment of the invention, to enhance the observability of the material condition, a state sensitive coating can be applied to the landing gear. In one embodiment of the invention, this coating is an austenitic stainless steel that is initially nonmagnetic but can become magnetic as the condition changes. In another embodiment of the invention, the coating is a dielectric coating that is monitored with a dielectric sensor.

In yet another embodiment of the invention, the shot peen quality if a nominally nonmagnetic material is monitored by measuring a magnetic property of the material and correlating this property to the shot peen quality. These nonmagnetic materials, such as metals and alloys, are often described as paramagnetic, where the magnetic susceptibility is small, or diamagnetic, where the susceptibility is negative. The shot peening process can produce a small but measurable change in the magnetic properties of such materials. In one embodiment of the invention, the relative permeability of the material is less than 1.05. In another embodiment of the invention, the magnetic property is measured by an eddy current sensor array. In one embodiment of the invention, the magnetic property is measured at more than one excitation frequency. In alternative embodiments of the invention, the magnetic property being measured is the relative magnetic permeability or the magnetic susceptibility.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS OF THE INVENTION

Figure 1:
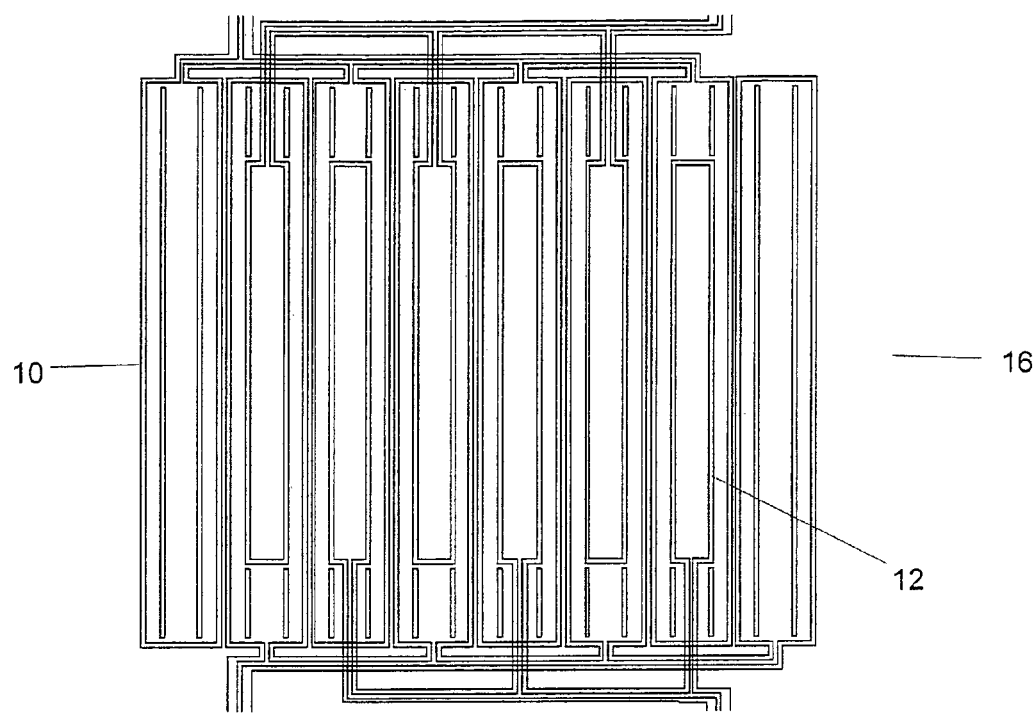
FIG. 1 is an illustration of a spatially periodic field eddy-current sensor.

Materials may be used and modified specifically for their capability to improve the observability of damage precursor, damage and usage states, or the occurrence of events. These self-monitoring materials (SMMs) exhibit changes in electrical, thermal, or other continuum properties that can be observed using remote or non-contact sensing methodologies. The properties of these materials, such as electrical conductivity, magnetic permeability or dielectric constant, vary with precursor, damage, usage or event states. Precursor states include residual stress, surface finish, coating thickness and porosity, and microstructure. Damage states include fatigue, thermal degradation and creep. Usage includes temperature, vibration and stress. Event states include those caused by overload, overtemperature or operational upsets. Information gained from observing these states via changes in the SMMs can then be used to address health control of the components, such as reworking or repairing the components.

Representative applications of these self-monitoring materials include propulsion systems and airframe structures. The use of magnetic field or eddy current sensors for characterizing material properties such as stresses has been described, for example in U.S. patent application Ser. No. 10/441,976, filed on May 20, 2003, the entire teachings of which are incorporated herein by reference. Here, the SMMs are used to enhance observability of a material conditions and can be used as coatings, dopants, or material replacements if the integrity of the component is not compromised by this replacement or modification. The properties of these SMMS are designed and/or selected to be sensitive to the states or conditions of interest.

Enhancing the observability of material conditions may greatly improve the efficacy of nondestructive examinations and the decisions based on these inspections. For both legacy and new aircraft platforms, the goal is to reduce sustainment costs while maintaining a high level of operational readiness. This includes onboard diagnostics for monitoring of damage progression and detection of cracks. Increasingly, damage tolerance methods are being used as predictive tools for crack growth to set inspection intervals to reduce premature component retirements.

These damage tolerance methodologies assume an initial crack size, just below the detection threshold of available inspection methods. To support these methods and more advanced methods as described in U.S. patent application Ser. No. 10/765,573, filed on Jan. 22, 2004, the entire teachings of which are incorporated herein by reference, increasing the observability of damage precursor states as well as any damage itself can improve assessment of the material condition and the application of the damage tolerance methods. This observability can be enhanced by the use of SMMs that have a significant measurable property change (e.g., magnetic permeability or electrical conductivity) in response to a precursor state change (e.g., residual stress), either as component elements themselves, coatings or as dopants or additives to the original base material of the component.

The principal distinction between precursor states and damage states is that precursor states result from manufacturing processes and rework/repair events. Characterization of these states may introduce requirements for quality assessment beyond typical practices. Some precursor states, e.g., inadequate residual stress, may be further modified by subsequent in-service damage. For example, a shot peened or otherwise cold worked structural component might have been cold worked to extend high cycle fatigue life, but in practice substantial low cycle fatigue contribution may result in stress relaxation, making the component more susceptible to fatigue crack initiation and propagation. In some applications, gradual or sudden changes of such precursor states may provide the only sufficiently early warning of subsequent failure, when, for example, time between crack initiation and failure is short. This might be the case in a landing gear where a previous overload event, e.g., hard landing, changed the precursor states, e.g., residual stresses, without producing a detectable crack. The next overload event may then result in a failure of the component.

A number of "non-magnetic" steels, metal, and alloys have two properties that lend themselves to self monitoring capability. One is anisotropy, which allows the directionality of the material property to be determined and correlated with precursor states. A second is a low but significant magnetic relative permeability (e.g., 1.005 to 1.02). An ability to measure and monitor changes of permeability in these strong paramagnetic materials enables measurement of stresses, including residual stresses (e.g., produced by shot peening or laser welding) and potentially offers the capability to monitor precrack fatigue damage. It may also be possible to produce new customized alloys, including titanium alloys that have solutes, e.g., iron, that increase the magnetic permeability so that the material combination has greater sensitivity to stress variations or precrack fatigue damage or thermal damage or other damage mechanisms. The alloys may also be functionally graded so that the enabling solute concentrations may be increased only near the surface for components at fatigue critical locations. This would improve shot peen quality control and precrack fatigue monitoring for those locations. Similarly, manufacturing processes such as welding or laser additive machining may be used to repair or fabricate components with enabling solutes added to alter local or global properties to increase the alloy or component self monitoring capabilities. Increasing the solute content at the surface near fatigue critical locations or locations where residual stress must be controlled could then assist in enhancing fatigue life.

SMMs may also be applied as coatings. A permeable layer (e.g., cobalt or a Heusler alloy) can be deposited on a substrate to provide the capability to measure stress or temperature independently and/or with higher sensitivity at higher temperatures. For example, cobalt has a higher Curie temperature than nickel. At temperatures of up to about 1100 degrees Celsius, the cobalt will remain ferromagnetic while the nickel at temperatures above 358° C. will not. Since permeability varies with stress, deposition of a cobalt layer on a nickel substrate will permit remote measurement of stress in the cobalt layer even through the nickel. It will also permit measurement temperature in the nickel independent of the stress since conductivity does not vary substantially with stress. Such layers may be embedded in devices such as fuel cells or gas turbine engines to permit measurement of both temperature and stress on surfaces at difficult-to-access or embedded locations, such as the inlet temperature and stress for a gas turbine engine or within the high pressure region of a gas turbine, or the residual stress and temperature at an interface in a fuel cell.

An important consideration for the design and/or selection of the SMMs is the measurement capability of the sensors or sensor arrays being used for the inspections. Note that the term inspections is not limited to the occasional or periodic scanning of a sensor over a surface and includes monitoring the response from surface mounted sensors either continuously or periodically. A conformable eddy-current sensor suitable for these measurements, the Meandering Winding Magnetometer (MWM®), is described in U.S. Pat. Nos. 5,015,951, 5,453,689, and 5,793,206. The entire teachings of these patents are incorporated herein by reference. The MWM is a "planar," conformable eddy-current sensor that was designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). MWM sensors and MWM-Arrays can be used for a number of applications, including fatigue monitoring and inspection of structural components for detection of flaws, degradation and microstructural variations as well as for characterization of coatings and process-induced surface layers. Characteristics of these sensors and sensor arrays include directional multi-frequency magnetic permeability or electrical conductivity measurements over a wide range of frequencies, e.g., from 250 Hz to 40 MHz with the same MWM sensor or MWM-Array, high-resolution imaging of measured permeability or conductivity, rapid permeability or conductivity measurements with or without a contact with the surface, and a measurement capability on complex surfaces with a hand-held probe or with an automated scanner. This allows the assessment of applied and residual stresses as well as permeability variations in a component introduced from processes such as grinding operations.

FIG. 1 illustrates the basic geometry of an the MWM sensor 16, a detailed description of which is given in U.S. Pat. Nos. 5,453,689, 5,793,206, and 6,188,218 and U.S. patent application Ser. Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength λ. A current is applied to the primary winding to create a magnetic field and the response of the MUT to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength λ. For an MWM-Array, the responses from individual or combinations of the secondary windings can be used to provide a plurality of sense signals for a single primary winding construct as described in U.S. Pat. No. 5,793,206 and Re. 36,986.

Figure 2:
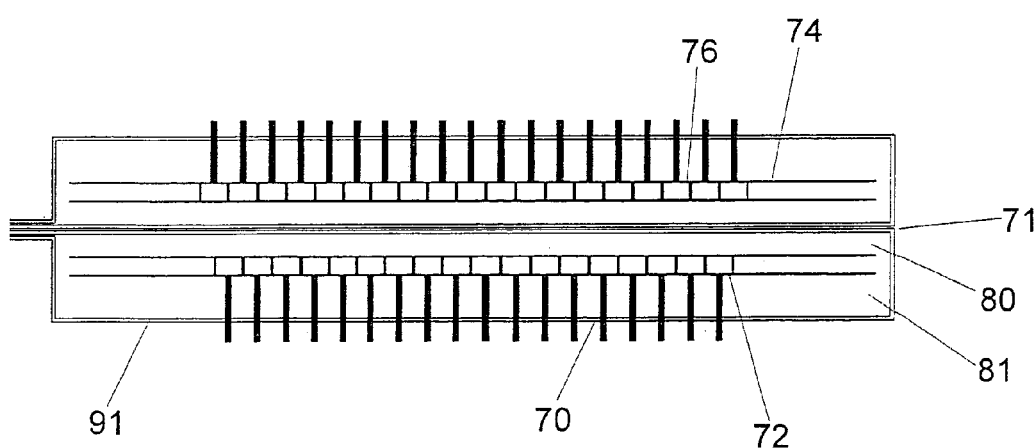
FIG. 2 is an expanded view of the drive and sense elements for an eddy-current array having offset rows of sensing elements.
Figure 3:
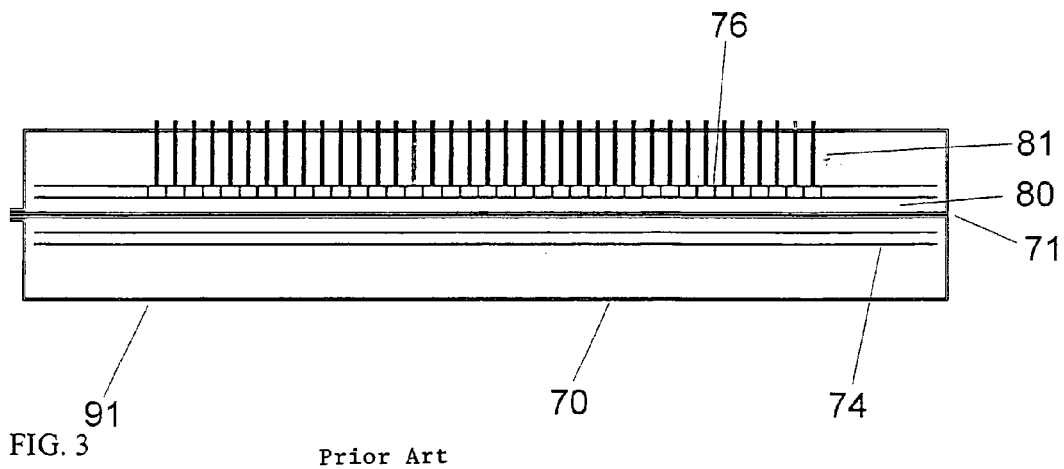
FIG. 3 is an expanded view of the drive and sense elements for an eddy-current array having a single row of sensing elements.
Figure 4:
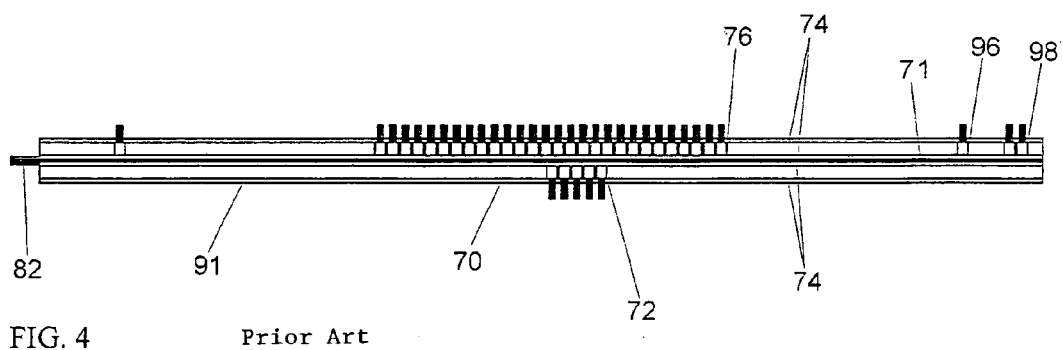
FIG. 4 is an expanded view of an eddy-current array where the locations of the sensing elements along the array are staggered.

The MWM-Arrays typically have one or more drive windings, possibly a single rectangle, and multiple sensing elements for inspecting the test material. Example sensor arrays are shown in FIG. 2 through FIG. 4 some embodiments of which are described in detail in U.S. patent application Ser. No. 10/102,620, filed Mar. 19, 2002, and Ser. No. 10/010,062, filed Mar. 13, 2001, the entire teachings of which are incorporated herein by reference. These arrays include a primary winding 70 having extended portions for creating the magnetic field and a plurality of secondary elements 76 within the primary winding for sensing the response to the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218. When the sensor is scanned across a part or when a crack propagates across the sensor, perpendicular to the extended portions of the primary winding, secondary elements 72 in a primary winding loop adjacent to the first array of sense elements 76 provide a complementary measurement of the part properties. These arrays of secondary elements 72 can be aligned with the first array of elements 76 so that images of the material properties will be duplicated by the second array (improving signal-to-noise through combining the responses or providing sensitivity on opposite sides of a feature such as a fastener as described in—U.S. patent application Ser. Nos. 10/102, 620 and 10/010,062. Alternatively, to provide complete coverage when the sensor is scanned across a part the sensing elements, can be offset along the length of the primary loop or when a crack propagates across the sensor, perpendicular to the extended portions of the primary winding, as illustrated in FIG. 2.

The dimensions for the sensor array geometry and the placement of the sensing elements can be adjusted to improve sensitivity for a specific inspection. For example, the effective spatial wavelength or four times the distance 80 between the central conductors 71 and the sensing elements 72 can be altered to adjust the sensitivity of a measurement for a particular inspection. For the sensor array of FIG. 2, the distance 80 between the secondary elements 72 and the central conductors 71 is smaller than the distance 81 between the sensing elements 72 and the return conductor 91. An optimum response can be determined with models, empirically, or with some combination of the two. An example of a modified sensor design is shown FIG. 3. In this sensor array, all of the sensing elements 76 are on one side of the central drive windings 71. The size of the sensing elements and the gap distance 80 to the central drive windings 71 are the same as in the sensor array of FIG. 2. However, the distance 81 to the return of the drive winding has been increased, as has the drive winding width to accommodate the additional elements in the single row of elements. Increasing the distance to the return reduces the size of the response when the return crosses a feature of interest such as a crack. Another example of a modified design is shown in FIG. 4. Here, most of the sensing elements 76 are located in a single row to provide the basic image of the material properties. A small number of sensing elements 72 are offset from this row to create a higher image resolution in a specific location.

Figure 5:
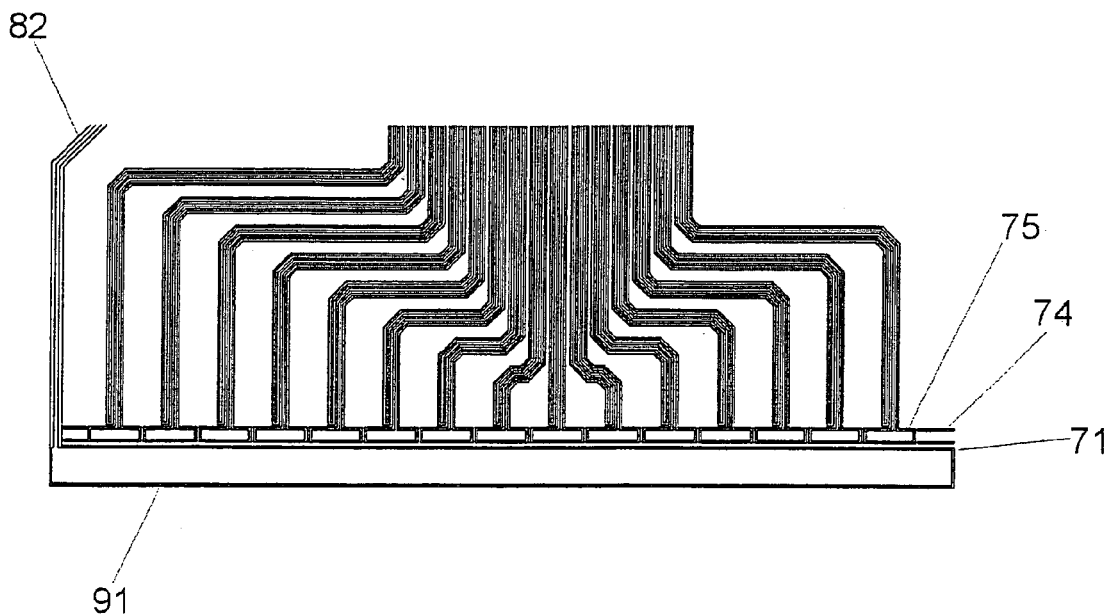
FIG. 5 is an expanded view of an eddy current array with a single rectangular loop drive winding and a linear row of sense elements on the outside of the extended portion of the loop.

The number of conductors used in the primary winding can be reduced further so that a single rectangular drive is used. As shown in FIG. 5, a single loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. This distance can be optimized using models to maximize sensitivity to a feature of interest such as a buried crack or stress at a specific depth. Advantages of the design in FIG. 5 include a narrow drive and sense structure that allows measurements close to material edges and non-crossing conductor pathways so that a single layer design can be used with all of the conductors in the sensing region in the same plane. The width of the conductor 91 farthest from the sensing elements can be made wider in order to reduce any ohmic heating from large currents being driven through the drive winding.

The MWM sensor and sensor array structure can be produced using micro-fabrication techniques typically employed in integrated circuit and flexible circuit manufacture. This results in highly reliable and highly repeatable (i.e., essentially identical) sensors, which has inherent advantages over the coils used in conventional eddy-current sensors. The lack of reproducibility with conventional coils introduces severe requirements for calibration of the sensors (e.g., matched sensor/calibration block sets). In contrast, duplicate MWM sensor tips have nearly identical magnetic field distributions around the windings as standard microfabrication (etching) techniques have both high spatial reproducibility and resolution. As the sensor was also designed to produce a spatially periodic magnetic field in the MUT, the sensor response can be accurately modeled which dramatically reduces calibration requirements. For example, calibration in air can be used to measure an absolute electrical conductivity without calibration standards, which makes the sensor geometry well-suited to surface mounted or embedded applications where calibration requirements will be necessarily relaxed.

For measuring the response of the individual sensing elements in an array, multiplexing between the elements can be performed. However, this can significantly reduce the data acquisition rate so a more preferably approach is to use an impedance measurement architecture that effectively allows the acquisition of data from all of the sense elements in parallel. Furthermore, ability to measure the MUT properties at multiple frequencies extends the capability of the inspection to better characterize the material and/or geometric properties under investigation. This type of instrument is described in detail in U.S. patent application Ser. No. 10/155,887, filed May 23, 2002, the entire teachings of which are incorporated herein by reference. The use of multiple sensing elements with one meandering drive and parallel architecture measurement instrumentation then permits high image resolution in real-time and sensitivity with relatively deep penetration of fields into MUT.

An efficient method for converting the response of the MWM sensor into material or geometric properties is to use grid measurement methods. These methods map two known values, such as the magnitude and phase or real and imaginary parts of the sensor impedance, into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 6:
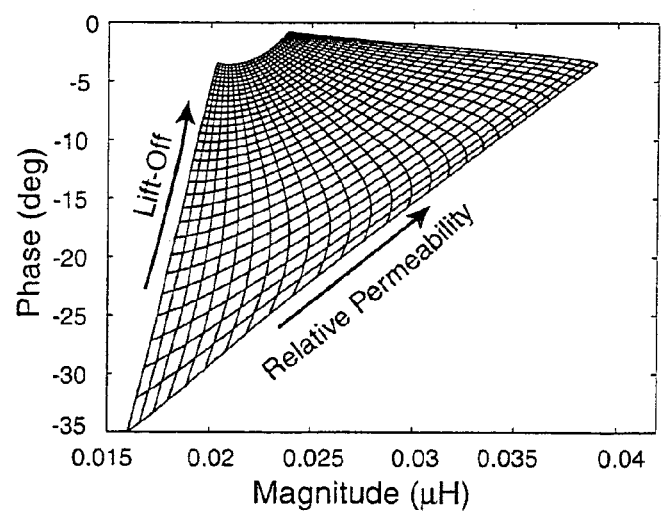
FIG. 6 illustrates a representative measurement grid relating the magnitude and phase of the sensor terminal impedance to the lift-off and magnetic permeability.
Figure 7:
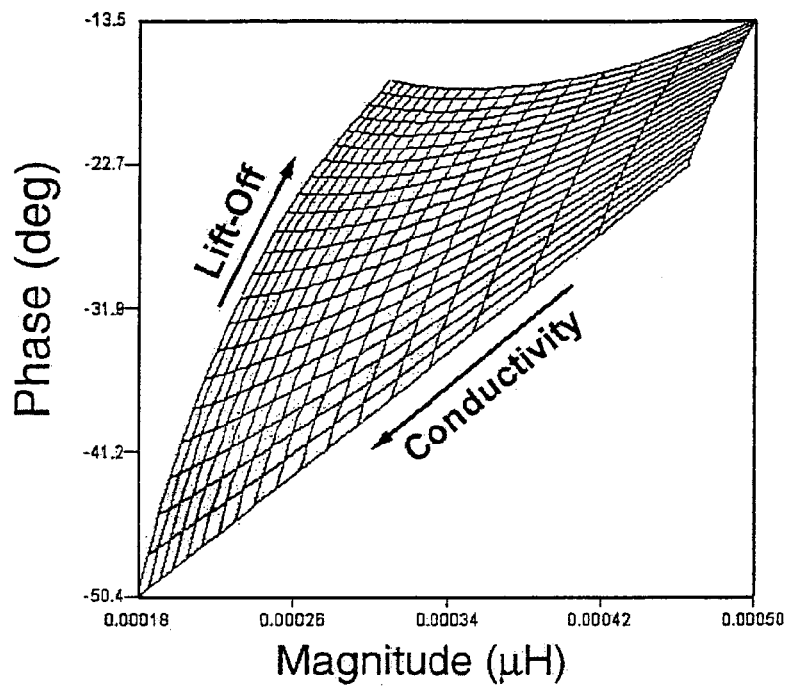
FIG. 7 illustrates a representative measurement grid relating the magnitude and phase of the sensor terminal impedance to the lift-off and electrical conductivity.

For ferromagnetic materials, such as most steels, a measurement grid can provide a conversion of raw data to magnetic permeability and lift-off. A representative measurement grid for ferromagnetic materials is illustrated in FIG. 6. A representative measurement grid for a low-conductivity nonmagnetic alloy (e.g., titanium alloys, some superalloys, and austenitic stainless steels) is illustrated in FIG. 7. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. The variation in the coating can be corrected at each point in the image to improve the measurement of permeability in the substrate for the purpose of imaging stresses.

Figure 8:
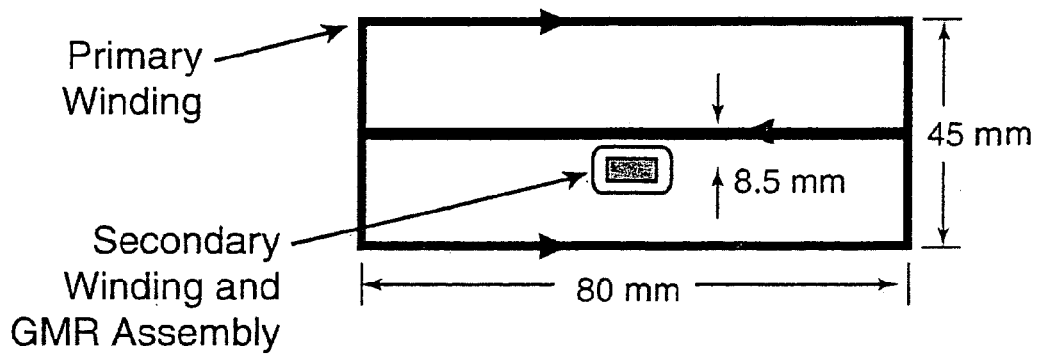
FIG. 8 illustrates a layout for a single turn Cartesian geometry GMR magnetometer.
Figure 9:
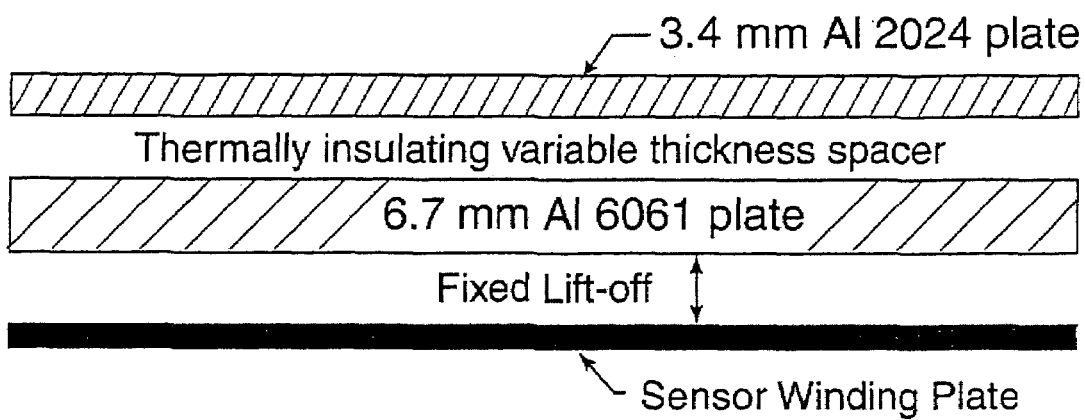
FIG. 9 illustrates a schematic for remotely monitoring the temperature of a plate.

In addition to inductive coils, other types of sensing elements, such as Hall effect sensors, magnetoresistive sensors, SQUIDS, and giant magnetoresistive (GMR) devices, can also be used for the measurements. The use of GMR sensors for characterization of materials is described in more detail in U.S. patent application Ser. No. 10/045,650, filed Nov. 8, 2001, the entire teachings of which are incorporated herein by reference. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations. An example rectangular or Cartesian-geometry GMR-based magnetometer is illustrated in FIG. 8. One example application using a GMR sensor is for monitoring properties through intermediate layers of metal. In this case, the absolute electrical properties are measured through thick metal plates and then related to other physical properties of interest. FIG. 9 shows one such layered geometry, with a low frequency (100 Hz) measurement used to remotely monitor the temperature dependent conductivity variation of an aluminum plate through a 6.3 mm (0.25 in.) thick aluminum plate. The thickness of the upper plate (remote from the sensor), the conductivity and thickness of the bottom plate (near the sensor), as well as its lift-off (proximity) from the sensor windings, are incorporated in the model used to generate the appropriate measurement grids. The two unknown properties monitored during testing were the conductivity of the upper plate and the thickness of the thermally insulating nonconducting spacer between the two plates, which also varied significantly with the temperature of the upper plate. The ability to measure the two unknown parameters independently was demonstrated by taking measurements at room temperature with spacers of varying thickness and observing that the data follow a constant-conductivity line in the grid. Similar measurements were performed to monitor stress variations on a hidden steel layer in a thick structure.

Figure 10:
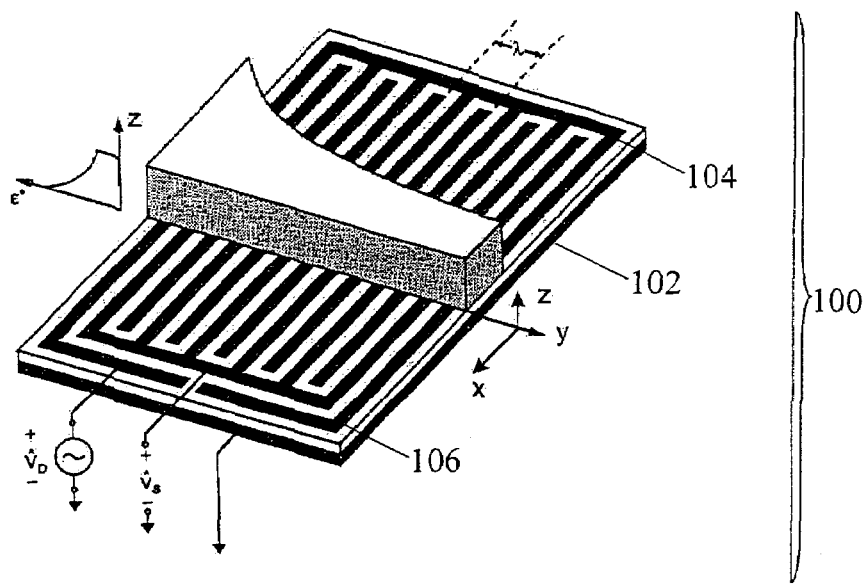
FIG. 10 illustrates a representative single wavelength interdigitated electrode dielectrometer with spatially periodic driven and sensing electrodes of wavelength □ that can measure dielectric properties of the adjacent material.

For insulating or weakly conducting materials such as fiberglass composites, capacitive or dielectric sensors can be used. The sensors are the electromagnetic dual to the inductive sensors, with electric fields taking the place of magnetic fields for inspecting the materials and can be used to monitor stress or temperature, moisture content or contamination or overload of fatigue in adhesives, epoxies, glass, oil, plastics and in single or multiple layered media. Here the conductivity and dielectric constant or complex permittivity and layer thicknesses are measured using the same methods as for magnetic field sensing. In one such electric field method multiple layers of material are added to a base material with each layer sensitive to different chemicals or biological materials. A representative single sided sensor geometry is shown in FIG. 10. The application of a sinusoidally time varying potential of angular frequency $\omega=2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, and 6,486,673 and in U.S. patent application Ser. No. 10/040,797, filed Jan 7, 2002, and Ser. No. 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $v_D$ while the other, 106, is connected to a high-impedance buffer used to measure the magnitude and phase of the floating potential $v_S$ or to a virtually grounded amplifier to measure the magnitude and phase of the terminal current I. The periodicity of the electrode structure is denoted by the spatial wavelength $\lambda=2\pi/k$, where k is the wavenumber.

When using magnetic field sensors, robust directional magnetic permeability measurements possible with MWM sensors and MWM-Arrays with grid methods allow estimation of stresses by taking advantage of the magnetostriction effect. For steels, at magnetic fields typical of those used for MWM, the magnetostriction coefficient generally is positive, so that the magnetic permeability increases with stress. Thus, once a correlation between stress and MWM measured magnetic permeability is established, stresses can be estimated as long as baseline information is available. Bias fields or DC offsets in the drive current (possibly using a multiple turn wound or etched drive winding) can also be used to move up the B-H curve away from the zero field location to improve performance.

Figure 11:
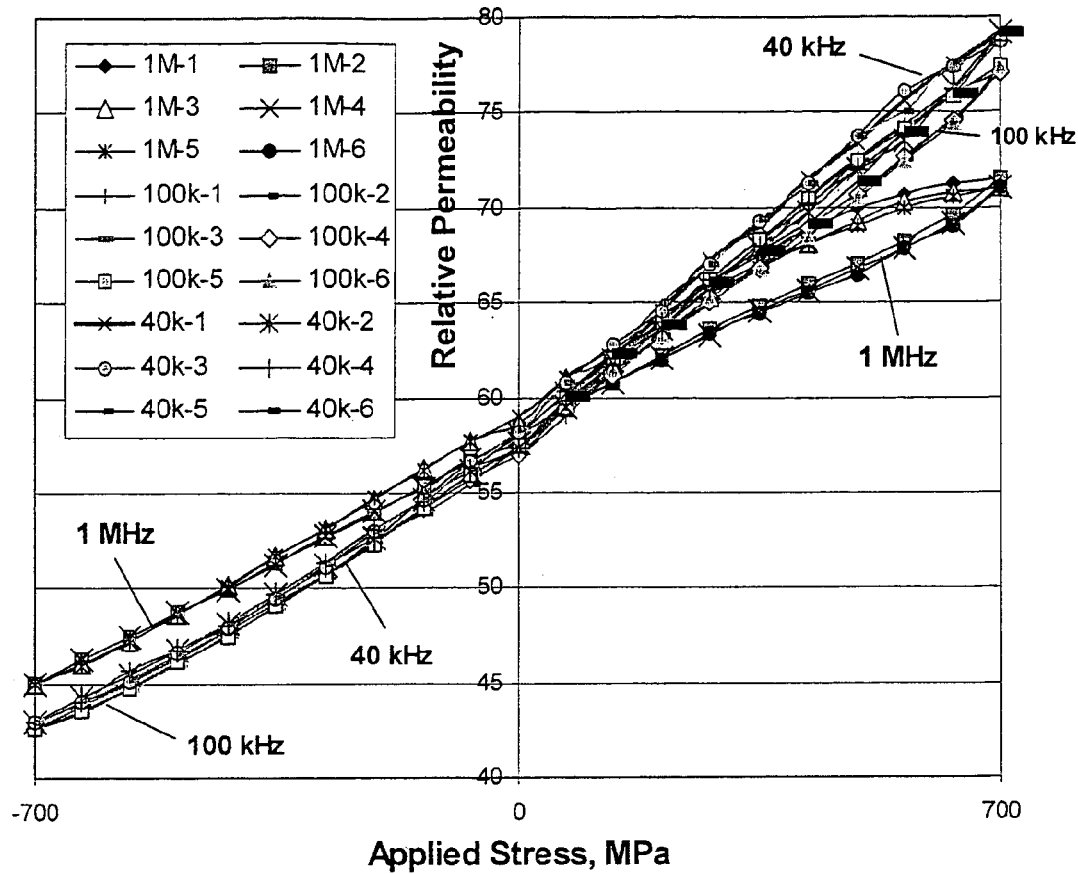
FIG. 11 illustrates the MWM measured magnetic permeability versus bending stress in a shot peened high-strength steel specimen at stresses from −700 to 700 MPa.

MWM permeability measurements on 300M high-strength steel specimens under fully reversed bending loading illustrate a correlation between the permeability and stress. The tests were performed on flat shot-peened specimens installed in a bending fixture. The stress range used in the test was between −700 MPa in compression and 700 MPa in tension. The stresses were determined from strains measured with a BLH strain gage using BLH instrumentation. The strain gages were attached to the "back" side. MWM magnetic permeability measurements were performed with the longer segments of the MWM drive winding perpendicular to the bending stress direction. In this orientation, the MWM measures permeability in the specimen longitudinal direction. FIG. 11 shows how the permeability measured at frequencies of 40 kHz, 100 kHz, and 1 MHz changes with applied bending stress. The data illustrate the sensitivity and quality of the permeability measurements for stress measurements in high strength steels over a wide range of stresses. The results clearly show the sensitivity to stress changes and reasonably small hysteresis, particularly in the compressive stress range.

The capability to perform directional permeability measurements allows characterization of both uniaxial and biaxial stresses, as described for example in U.S. patent application Ser. No. 10/351,978, filed Jan. 24, 2003, the entire teachings of which are incorporated herein by reference. In the latter case, the MWM permeability measurements at various sensor orientations reveal the directions of the principal stresses. Furthermore, permeability data from multiple frequency measurements can be used for reconstruction of stress distribution with depth. For typical excitation frequencies in the several kHz to several MHz range, the depth of penetration of the magnetic field is limited to a fairly thin layer near the surface, e.g., the first 0.5 mm (0.02 in.). However, lowering the excitation frequency and using alternative sensing elements such as GMR devices permit measurements to a significantly greater depth. Also, MWM-Arrays allow imaging of stress distributions over wide areas.

Figure 12:
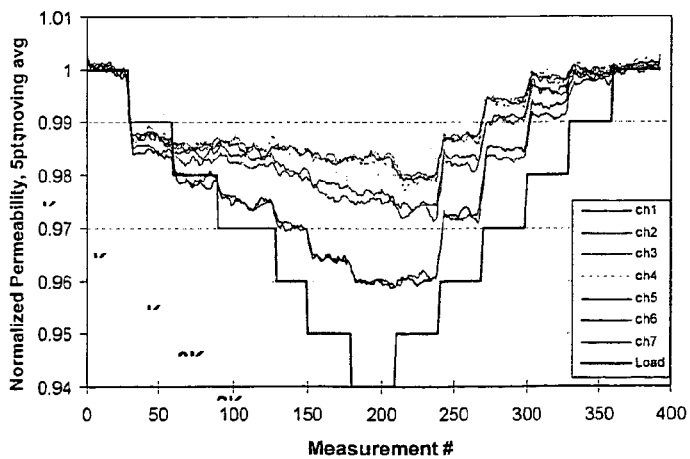
FIG. 12 illustrates MWM measured transverse permeability changes at incrementally increasing and decreasing tensile load (maximum load=53.4 kN (12,000 lbs); increment=8.9 kN (2,000 lbs)).

FIG. 12 shows the results of another set of tests illustrating the magnetic permeability changes due to the Poisson's effect or the transverse contraction under tensile axial load. A 7-channel MWM-Array was mounted on a specimen with the longer segments of the MWM-Array drive oriented along the specimen axis, i.e., parallel to tensile load orientation during tests, so that the magnetic permeability in the transverse direction is measured. In this test, the tensile load was first incrementally increased by 8.9 kN (2,000 lbs) to the maximun tensile load of 53.4 kN (12,000 lbs) and then incrementally decreased to 0. The estimated maximum axial stress in the center of the area was about 700 MPa (100 ksi). After each load increment, a constant load was maintained for a period of time. The loading pattern and MWM-Array measured transverse permeability in all seven channels is shown. The observed change in MWM-Array measured transverse permeability appears to mimic changes in transverse strain. The lowest permeability changes occur near the center. The results emphasize the importance of permeability measurements and suggest that bidirectional permeability measurements are critical to stress measurements even under uniaxial loading.

The ability to detect and image stress distributions has implications for the detection and imaging of early stage fatigue damage as well. Fatigue tests of 4340 steel specimens revealed the capability to detect precrack damage early in the fatigue life. These specimens were designed with a cylindrical cavity in the gage section, where an MWM-Array could be mounted, and reinforcement ribs on the back side. This provides a nonuniform stress distribution with the maximum stress in the central portion of the cavity, as verified by a finite element analysis, beneath the footprint of the MWM-Array. The shape and stress distribution within the cylindrical cavity can be varied to simulate the geometry of high strength steel components of interest. The MWM or MWM-Array sensors can be oriented with their longer winding segments aligned parallel or perpendicular to the direction of likely fatigue crack orientation. The sensor aligned perpendicular to this direction is most sensitive to fatigue damage and crack monitoring, while the sensor with longer drive segments parallel to this direction is most sensitive to stress (i.e., magnetic permeability is measured dominantly in the direction perpendicular to the longer drive segments, while conductivity, or induced current flow, is sensed dominantly parallel to the direction or the longer winding segments). Multiple series connected or multiplexed eddy current sensors, such as MWM-Arrays, can be mounted at selected critical and non critical locations to support both fatigue and stress monitoring either continuously or periodically or on a scheduled or unscheduled basis depending on convenience or loading/fatigue/overload events.

Figure 13:
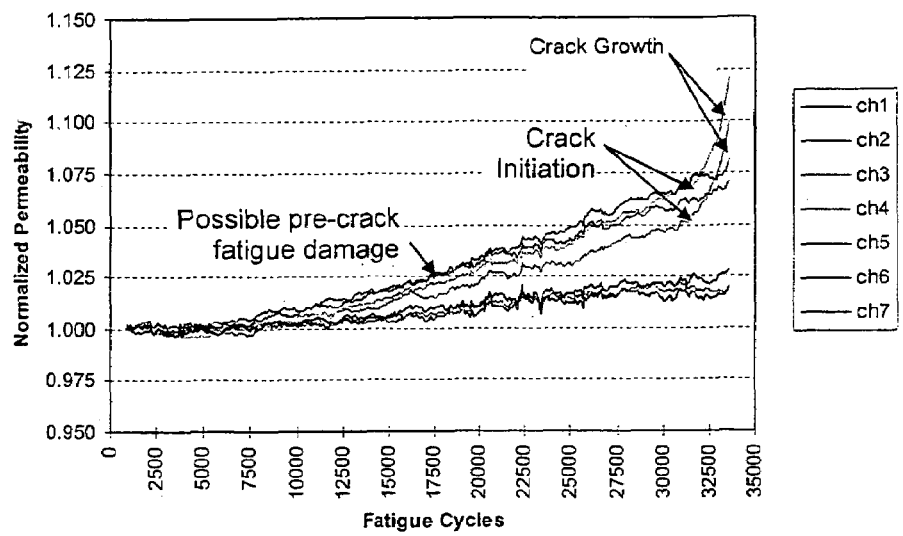
FIG. 13 illustrates a plot of normalized permeability against the number of fatigue cycles for a shot peened 4340 steel specimen.

FIG. 13 shows the permeability changes during another 7-channel MWM-Array test. There is virtually no change in the measured permeability up to 7,000 cycles. The change in the permeability slope in the four centrally located channels at about 7,000 cycles is most likely associated with residual stress relaxation and precrack fatigue damage. This fatigue damage stage extends, perhaps, up to 17,000 cycles followed by initiation and extension of multiple microcracks. Two of the channels show a significant permeability increase at 32,000 cycles indicating coalescence of closely spaced cracks and faster crack growth. SEM analysis on this specimen revealed a few small cracks, with the longest crack approximately 200 µm (0.008 in.) long. This crack was also confirmed by fluorescent liquid penetrant inspection (FPI). The FPI indication appeared as a tiny "speck" judged to be on the order of 0.25-mm (0.01-in.) long.

Figure 14:
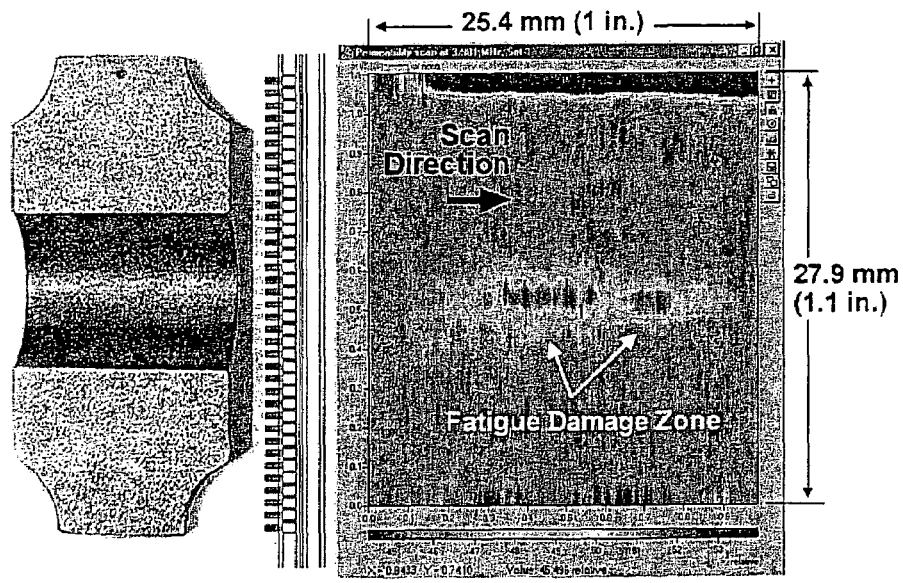
FIG. 14 illustrates an image of the MWM measured permeability of the fatigue damage zone at the end of the fatigue test.

The fatigue critical area of this specimen was also scanned with an imaging MWM-Array, with the drive oriented perpendicular to the axis of the coupon cavity. This orientation is perpendicular to anticipated predominant orientation of fatigue cracks, and is the same as in fatigue test monitoring of FIG. 13. FIG. 14 shows a permeability image and aligned intermittent regions of increased permeability having a combined length of about 20 mm (0.75-in.) Three of these regions appear to contain short indications characterized by the highest measured permeability. The other relatively high permeability regions are likely to indicate stress relaxation due to the cyclic loading and fatigue damage prior to formation of detectable cracks. These regions of enhanced permeability are also consistent with the higher stress region of the component from the finite element analysis.

Figure 15:
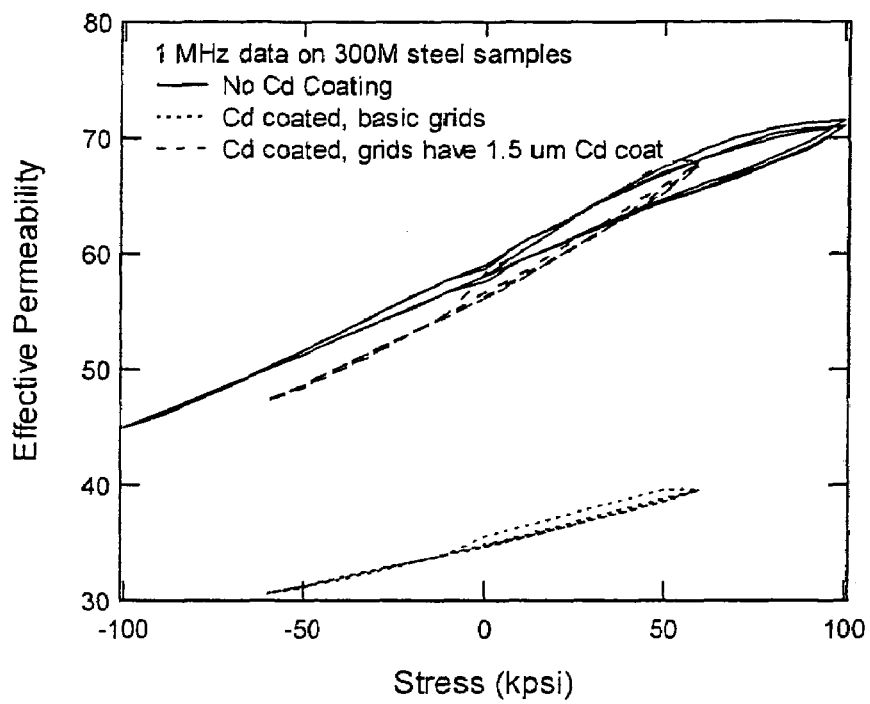
FIG. 15 illustrates the effective permeability variation with applied stress for coated and uncoated samples.

For cadmium-plated high-strength steel components, it is important to account for the effect of the cadmium layer. This is illustrated in FIG. 15, where a coating model was applied to the multiple frequency data obtained from MWM measurements on the 300M high strength steel specimens. Qualitatively, this data (from 39.8 kHz to 1 MHz) showed a decrease in the effective permeability and lift-off compared to measurements on the uncoated specimen. This is consistent with the presence of a nonmagnetic conducting surface layer on magnetizable substrate. The model assumed a Cd layer (electrical conductivity of 22% IACS, 12.76 MS/m) on top of a magnetizable substrate (electrical conductivity of 3.4% IACS, 2 MS/m), so that the unknowns in this model were the lift-off, Cd layer thickness, and permeability of the substrate (steel). The stress distribution, and hence the magnetic permeability, is not necessarily uniform with depth into the substrate and definitely not uniform for a shot peened steel. As the first step, the thickness of the Cd layer on an unstressed sample was estimated using a least-squares minimization routine on the multiple frequency data. A fast table lookup within a lattice could also be used. Assuming a substrate permeability of 57.1, the Cd thickness was estimate to be 1.5 µm. Using this thickness, substrate permeability/lift-off grids were then generated so that the effective permeability of the substrate could be determined. FIG. 15 shows permeability vs. stress curves for non-plated steel, for Cd-plated steel using a model that does not account for the Cd layer, and for Cd-plated steel using a model that does account for the Cd layer. As shown in FIG. 15, using grids that have a thin Cd layer can provide estimates of the permeability that are similar between the coated and uncoated samples. Without this compensation for the presence of the Cd coating, the permeability estimates are significantly reduced for the coated sample.

The numerical value for the Cd layer thickness of 1.5 µm is small compared to the nominal thickness of 10–20 µm because of the assumed conductivity for the layer. For these relatively thin layers and intermediate excitation frequencies, the measurements are essentially sensitive to the product of the layer thickness and electrical conductivity. For alloy layers (e.g., cadmium-titanium alloys) or for microstructural variations due, for example, from porosity introduced during the coating process, the electrical conductivity can be lower, in the range of 1.2–7.0 MS/m (2–12% IACS) and the corresponding thickness larger. The thicker Cd layer values can be accommodated, without appreciably affecting the permeability estimates, if a lower conductivity is used for the Cd layer.

MWM-Arrays can also be used in a surface mounted or even non contact (where lift-off is measured using grid methods) to monitor stress and proximity (or vibrations). As with strain gages or extensometers this information can be used to control load frames, monitor changes in material properties or structures, or monitor in service behavior and damage. Integration of information with that from strain gages or extensometers can be used to support decisions regarding fitness for service, material life or to assess material performance in fatigue tests.

Figure 16:
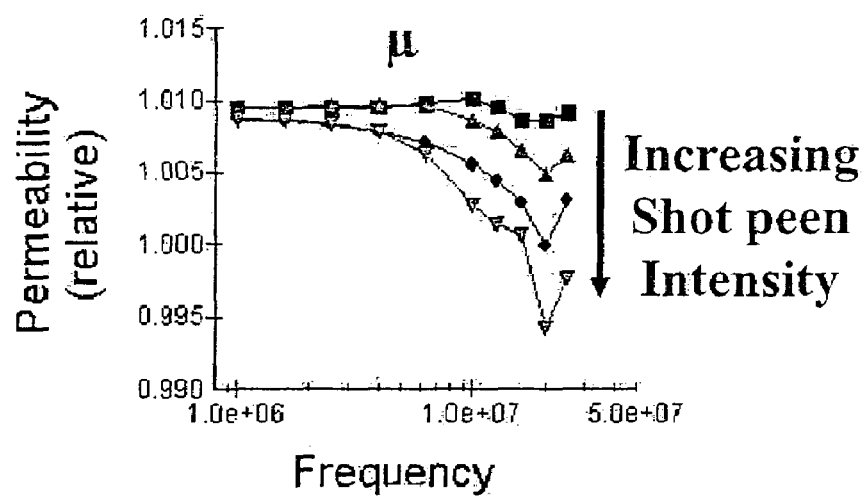
FIG. 16 illustrates an effective permeability plot as the frequency and shot peen intensity is varied assuming a constant conductivity.
Figure 17:
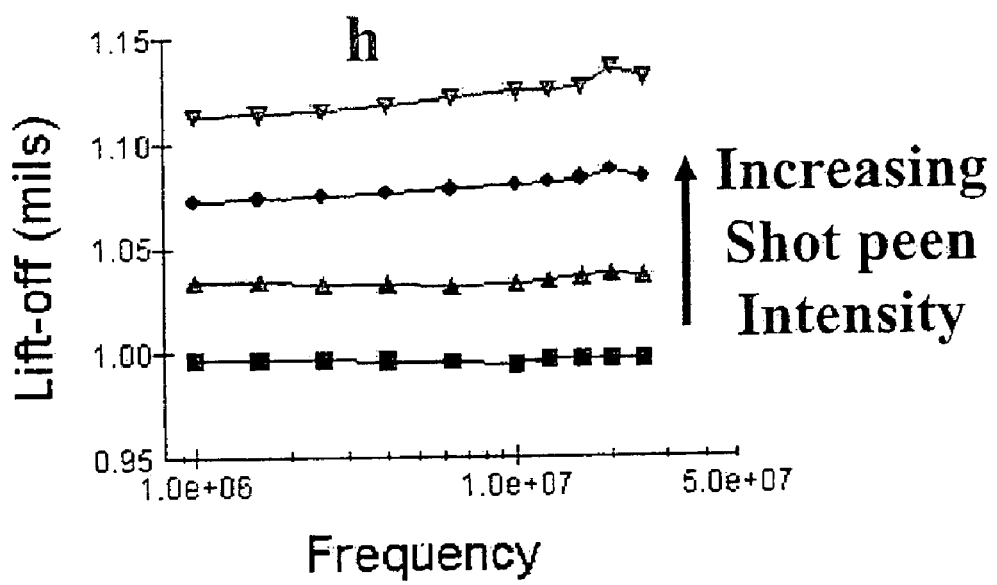
FIG. 17 illustrates an effective lift-off plot as the frequency and shot peen intensity is varied assuming a constant conductivity.
Figure 18:
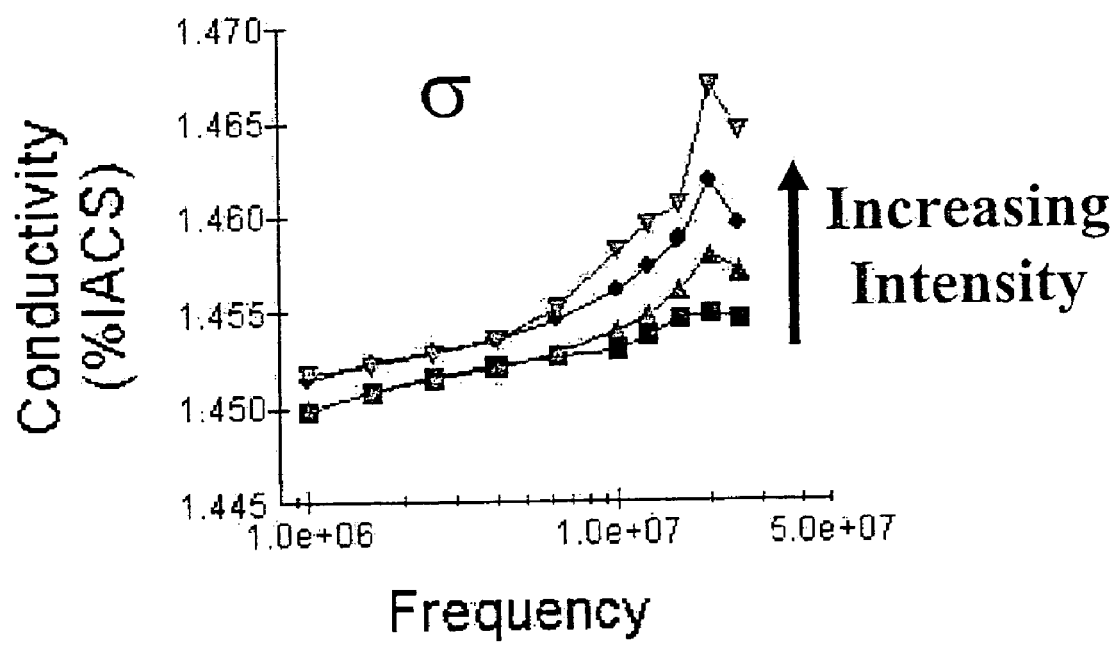
FIG. 18 illustrates an effective conductivity plot as the frequency and shot peen intensity is varied assuming a constant permeability.

Another aspect of this invention is the modification or selection of materials that have properties which change with processing conditions such as shot peening or heat treatment. As examples, shot peening of nickel alloy engine materials, such as Alloy 738 or Alloy 718, or titanium and titanium alloys, may produce near surface relative permeability or electrical conductivity variations. These materials are nominally nonmagnetic, being paramagnetic with a relative permeability less than about 1.05 or diamagnetic. For one such alloy, assuming a constant conductivity, the permeability (FIG. 16) and lift-off (FIG. 17) varies with the shot peen intensity. If a constant permeability is assumed, then the effective conductivity (FIG. 18) varies with the shot peen intensity. At sufficiently high frequencies, the magnetic field is confined near the surface of the MUT and reflects mainly the stress of the surface region. At lower frequencies, the magnetic field can penetrate through this region and the average or effective property (permeability or conductivity) approaches the bulk value. Doping of the material near the surface to enhance these effects, by adding magnetizable material for the permeability or good electrical conductors for the conductivity, may enhance this response and the observability for health control actions. High resolution images of permeability can be used to map residual stress variations to qualify shot peening or other manufacturing processes or to assess material aging and degradation. Then, regions with unacceptable residual stresses might be reworked (e.g., blending and reshot peening) to extend life. Using such multiple frequency information permits the independent estimation of electrical conductivity and permeability of nominally nonmagnetic alloys, including some titanium alloys, for damage or quality control assessment.

In a similar fashion, weld quality in strongly paramagnetic alloys can be assessed at single or multiple frequencies using measurements at one location or multiple locations before, after and even during welding. This will permit mapping or point measurement of residual stress variations in these alloys caused by welding. In one embodiment of the invention, during processing, e.g., welding, the permeability is monitored in neighboring material to assess the stress variations with cooling etc. In another embodiment, the enabling solutes are added during welding to increase the sensitivity to stress variations. For example, permeability may be increased by laser welding with one or more additives so that stress mapping is possible at the weld.

To enhance observability of the condition or degradation of a component, the component material may be replaced with a self monitoring material. This would permit management of fatigue critical components by using materials that provide early warning of damage. By replacing entire components or critical areas of components with parts fabricated from early warning or self-monitoring materials, the components can fail in a "gracefully" aging mode that is observable. Some components, such as landing gear, are already made from such SMMs but other flight critical components such as wing attach fittings can be considered. For example, one or more wing attach fittings or fasteners on each aircraft in the fleet or on selected aircraft could be replaced with an austenitic stainless steel, e.g., type 304 stainless steel or with an alternative material fitting. Either the entire fitting might be made from one of these materials or bushings might be inserted in critical fastener holes in existing or new fittings to extend their life by providing self monitoring capacity. Fabrication may include laser-additive manufacturing or other processes. This may include combinations of materials selected for strength with other materials selected for self-monitoring capacity to provide observability for fatigue, overload, etc.

This use of a second material is different than the common use of intermediate materials that enhance coupling between the sensor and an article. In the common usage, the measurement is still made on the article itself, not on the coating material, and the intermediate materials improve the sensor response. Here, measurements are made on the electrical property variation of the second material or on areas of the first material that are doped by the second material. As an example, thermally conducting pastes, that are typically electrically insulating as well, are commonly placed between the test material and temperature sensors, such as thermistors or thermocouples, to enhance the thermal conduction between the test material and the temperature sensor. Here the use of a second material would be measuring an electrical property variation of the coating that could then be related to the condition (e.g., temperature) of the article. As another example, adding a magnetic (permeable) coating to a conducting material may shift the resonance or response of the sensor to the conducting material so that conductivity may be more sensitive to the article condition.

Figure 19:
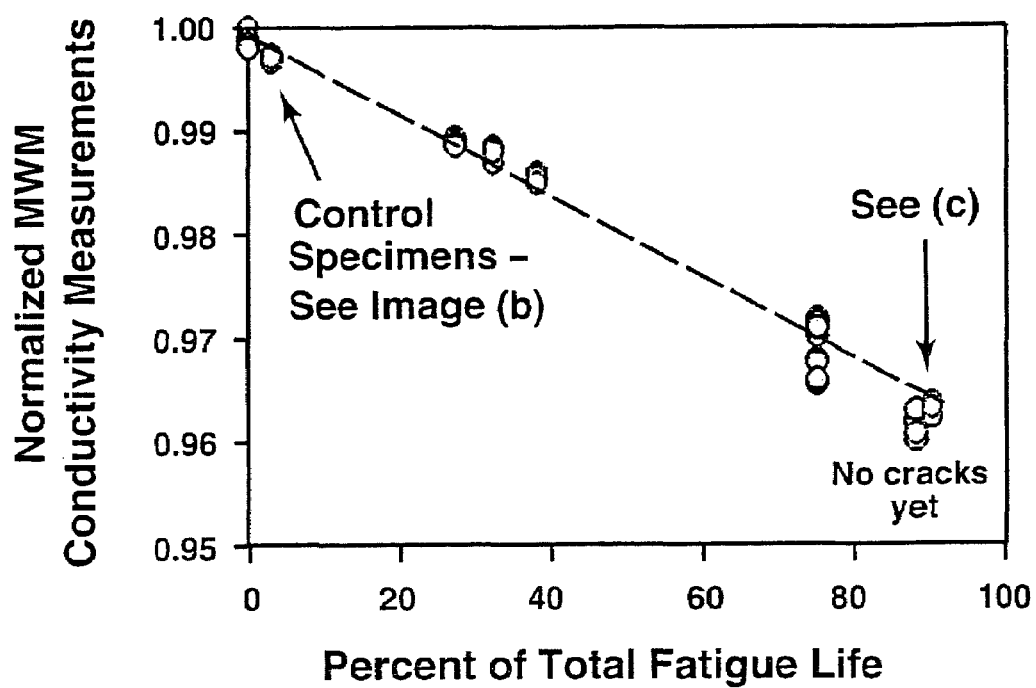
FIG. 19 illustrates the effective conductivity changes as a function of percent of fatigue life for Type 304 stainless steel.

FIG. 19 shows that progression of fatigue damage on type 304 stainless steel during life produces a nearly linear reduction in this effective property. Note this "effective conductivity change" is physically attributed to a permeability change. Each data point represents a different specimen. Each specimen was tested to a fraction of total life. The total life was determined as a mean number of cycles to failure in a separate set of specimens from the same lot of material. Both sets of specimens were tested under the same test conditions. Images of the magnetic permeability of the specimens illustrate that the fully annealed material has a relative magnetic permeability of 1.0 when not cyclically loaded, and the permeability is significantly greater than 1.0 as fatigue develops. Permanent magnet based sensors could also be used to determine when such as material has gone magnetizable and may be able to assess the degree of magnetization, relative permeability, or magnetic susceptibility.

These methods can also be applied to the remote temperature monitoring for gun barrels, engines, and other constructs, where an inductive drive winding located outside of gun barrel or engine is used to monitor the temperature. The response of the gun barrel or engine material is measured with one or more sense elements at single or multiple frequencies. The electrical properties of the gun barrel or engine case are measured along with layer thicknesses and sensor lift-off using model based (or grid) methods. The barrel or case can be modeled as one, two, or several layers with the electrical conductivity and/or the magnetic permeability of each layer being measured independently or assumed known. This enables the measurement of the internal temperature, independent of the external temperature. If necessary, a previously established correlation between the electrical property measurement and the temperature can be used.

To enhance this observability of this measurement, coatings can be placed on the inside of the gun barrel, engine, or other construct. This coating can enhance the sensitivity of the measurement to the internal temperature by using materials for which the conductivity or permeability varies substantially with temperature. The materials may be selected so that the Curie temperature is high enough to maintain sensitivity even at elevated temperatures. Similarly, stress may be monitored instead of temperature. For example, in a pipe or gas flow conduit, a coating highly sensitive to stress could be used. This layer could be a foam or other compressible layer that changes density with pressure to enable the local stress or pressure measurement. Again, a correlation between the electrical property measurement and the density of the coating may be necessary. This compressible layer may be a dielectric material for use with capacitive sensors or a magnetic or conducting material for used with magnetic or eddy current sensors.

The material of the article may also be processed so that the surface properties provide greater sensitivity to variations in the article condition than the original material properties of the article. For example, shot peening can introduce compressible residual stresses in the surface of the component. Thermal overload or exposure to elevated temperatures may cause stress relaxation in the article that can be monitored through stress dependent permeability changes. Similarly, laser welding or other such methods may be used to modify near surface layers.

Eddy current sensors and sensor arrays are well-suited to the measurement and monitoring of stresses (applied and residual) in steel components. The sensors can be used to inspect selected locations on a part by placing the sensor over the area of interest, scanning over the area, or permanently mounting or affixing the sensor to the surface. By measuring with multiple sensor orientations, the permeability and stress distribution can be inferred. Preferably, the orientations are perpendicular to one another so that the biaxial stress distribution is obtained. The anisotropy is most easily obtained when the orientation of the sensor or sensor array has the direction of greatest sensitivity aligned with the directions of the maximum and minimum principal stresses in the materials. When the sensors are flexible and can conform to the complex geometry surfaces, the sensors can be supported by a bottom foam support that makes the sensor essentially flat until placed onto the surface. Alternatively, the sensors can be molded into a fixture that conforms to or has a shape similar to the geometry of the test material.

These same techniques can be used to detect and characterize overload effects on components where excessive mechanical or thermal loading on a component can compromise the structural integrity of a component so that it fails during subsequent use. An example component is landing gear. During towing of aircraft, taxi events from turns, bumps, or similar circumstances, or hard landings, it is not unusual for a landing gear component or components to experience mechanical loads approaching or exceeding the elastic limit. Permanently mounted sensors (such as strain gauges or MWM-Arrays, UT sensors or Barkhausen sensors) can be used to monitor loads and detect overloading of the landing gear material during towing. In particular, since some landing gear components are made from high strength (magnetic) steels, permanently mounted eddy current sensors and arrays can be used to monitor the stress dependent permeability and the mechanical load or overload condition.

Figure 20:
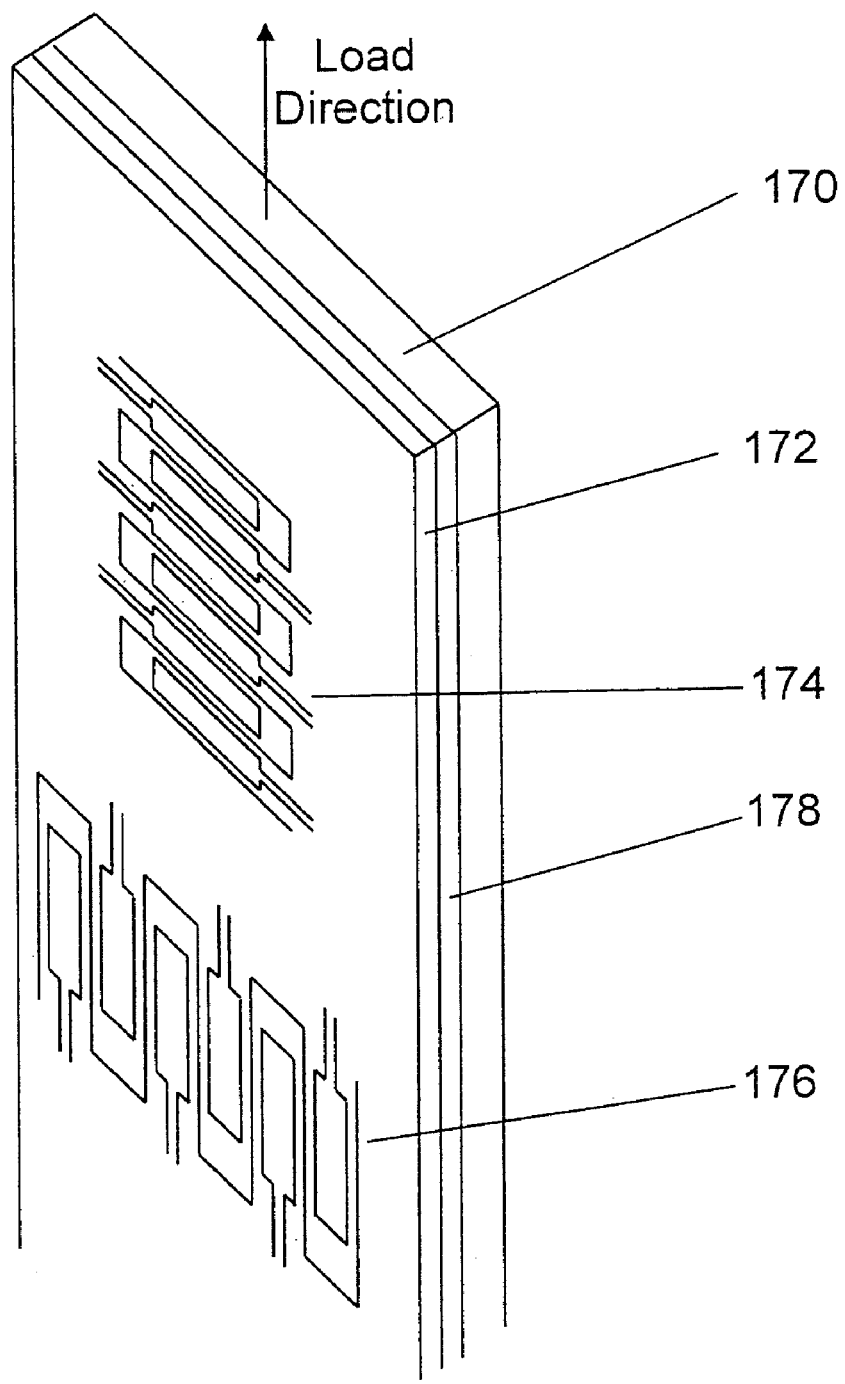
FIG. 20 illustrates a schematic drawing of two MWM-Arrays mounted to a test material surface and oriented in different directions relative to the load direction.

FIG. 20 shows an example measurement configuration. The substrate material 170 can be a flat or curved steel component that may also have a protective cadmium coating 172. The MWM-Array 174 is oriented so that the relative permeability measurements will be sensitive to the applied stress or load. The MWM-Array 176 is oriented so that the relative permeability measurements will be insensitive to the applied stress or load. If an overload event occurs than the residual stress distribution will change and the response of all of the sense elements may be altered. In particular, the non-load sensitive sense elements may shift due to the different residual stress distribution. Note that if the substrate material 170 is a nonmagnetic material such as an aluminum alloy or a brass, then the coating 172 can be a thin magnetizable coating, such as a cobalt coating 0.015 mm (0.0006 in.) thick. Then the sensor arrays will be sensitive to the permeability changes in the coating, which reflect the stress of the substrate. The coating does not need to cover the entire component and only needs to be in the area being sensed by the sensor. A second coating 178 or a third material may also be added, to the front or back surface of the test material. The different materials may also be sensitive to different properties. As an example, one layer may be more sensitive to stress while the other layer is more sensitive to temperature. Clearly, more materials could also be added.

Figure 21:
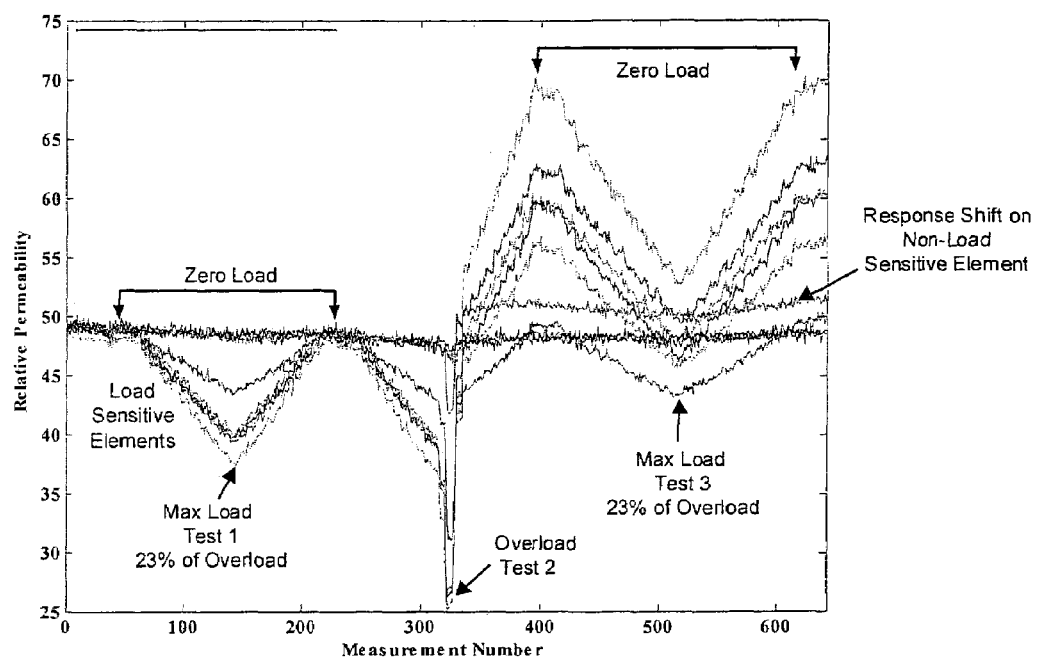
FIG. 21 illustrates a representative relative permeability plot for several sense elements for several applied load cycles, including an overload event.

As an example application, MWM-Arrays can be located at several locations on the landing gear in one or more orientations relative to possible applied loads during towing or taxiing. The sensors monitor the load and detect the onset and degree of overload. The load causes a change in the MWM-Array response, for example, the measured magnetic permeability. However, loads that produce local stresses within the elastic range leave no permanent change in the permeability, while higher loads, produce a permanent plastic deformation and changes in residual stresses. Furthermore, sensors oriented so that the permeability is measured in the direction perpendicular to the maximum principal stresses typically have limited sensitivity to the stress variation produced by the applied loads. Thus, these sensors detect the changes produced primarily by the overload. This can be seen in FIG. 21 where several MWM-Arrays were mounted on the curved surfaces of a landing gear component. Some of the sense elements were oriented to be sensitive to the applied load, while others were oriented to be insensitive to the applied load. During the first test, the elements oriented to be insensitive to the applied load did not change. However, after the overload event during test 2, one of the non-load sensitive sensing elements and most of the load sensitive sense elements indicate a (tensile) shift in the responses. This is attributed to a change in the residual stress distribution due to the overload event.

To monitor such events, a device is connected to either the permanently mounted sensors, or the device itself places sensors proximate to locations on the landing gear of interest. The device remains in place during towing or taxiing to monitor the loads and detect the onset and degree of overload. The sensors can be mounted onto the landing gear component or within a fixture that is connected to the landing gear. The towing operator can then be alerted if the stresses exceed an accepted limit or are progressing in that direction so that the towing parameters can be altered. This can involve an automatic adjustment within the towing mechanism either before an overload occurs or after the first overload to avoid subsequent overloads. If an abusive towing event is detected (e.g., an overload) then a scanning MWM-Array can be used to determine the degree of damage. This would require a previous baseline of the properties of each landing gear or a nominal set of similar gear components. Existing health monitoring sensors on the aircraft may also be used for this purpose, if appropriate. Then, the landing gear could be getting inspected each time the aircraft is towed.

SMMs or coatings can be used to enhance the observability of the stress changes and overload. These can be implemented in the tow-monitoring device or on the gear itself. For example, the coating can be made of an austenitic stainless steel. If an overload, fatigue, or thermal event occurs, the coating becomes magnetizable or more magnetizable. A simple magnet is used to determine if the coating has become magnetizable. If the coating has become magnetizable or showed stronger magnetization, then a scan is performed to determine the degree of magnetization and to support decisions regarding rework, repair, and assessment. For some coating materials, such as ferromagnetic metals or alloys that are at least partially annealed, the magnetic permeability can decrease with an overload or fatigue event. A simple array of magnets of other relatively simple sensor designs could be used to scan or measured at individual locations the coating condition to determine existence or occurrence of an event, or to monitor physical property changes. In a related embodiment, a heat treatment or another material condition control action is performed to "reset" the coating or self-monitoring material, so that it is no longer magnetizable to determine if another event will happen. The self-monitoring material or self-monitoring coating could also be made of a material whose dielectric properties change in response to an event or usage.

Another aspect of this invention is the recalibration in place for surface mounted sensors, for example for landing gear monitoring. If the sensor fails, recalibration can be performed by removing the sensor but not the cable between the sensor location and the impedance measurement instrumentation. A new sensor can be plugged into the cable and then attached to the surface. The old sensor standardization parameters (which can also be called calibration parameters), between the material properties and sensor response, can be used when the sensors or sensor arrays are reproducible. As another variation, the sensor and cable could both be replaced for a given landing gear location. To reduce the effect of any sensor or cable variations, the sensor should be standardized with measurements in air or with reference measurements on the landing gear material itself or another reference standard. However, in both cases, since the landing gear material has not changed, the original stress correlation with permeability at that location could still be used. This stress correlation, which could be in the form of a table, can be obtained when the sensor is first attached to the landing gear and controlled loads are applied to the structure. This could even be done in the factory and provides a calibration between the measured permeability and stress for that sensor location and load condition. After attaching the sensor, with or without a new cable, simply verifying that the permeability is appropriate for that location validates the recalibration.

While the inventions have been particularly shown and described with reference to preferred embodiments thereof, it will be understood to those skilled in the art that various changes in form and details may be made therein without departing from the spirit and scope of the invention as defined by the appended claims.

All U.S. patents and patent applications mentioned in this application are incorporated herein by reference. Additional references incorporated herein by reference in their entirety: Bozorth, R. M., Ferromagnetism, IEEE Press, 1978.

The following references are also incorporated herein by reference in their entirety.

1. NASA Phase I Proposal, titled "Propulsion System Life Management Through Enhanced Observability," Topic #A1.02, dated Sep. 8, 2003.
2. Army Phase I Proposal, titled "MWM-array Sensor Networks for Fatigue Monitoring of Army Aircraft," Topic #A03–071, dated Aug. 12, 2003.
3. Technical presentation titled "Landing Gear Inspection Opportunities Using Scanning and Permanently Mounted Eddy Current Sensor Arrays," ATA Conference 2003, Sep. 25, 2003.
4. Technical presentation titled "MWM Eddy-Current Sensor Arrays for Residual Stress Mapping," ASTM Symposium, Salt Lake City, Utah, May 19–20, 2004.
5. Technical presentation titled "High-Resolution Residual Stress Imaging Using MWM-Arrays with Pre-Computed Response Databases," QNDE Conference, Colorado School of Mines, July 2004.

What is claimed is:

1. A method of enhancing observability of an article condition said method comprising:
   processing a surface material of the article, the surface material having an electrical property, where the electrical property of the surface material experiences a larger variation in response to said condition experienced for the same variation in said condition than an unprocessed material, the larger variation enhancing observability of the article condition;
   measuring said electrical property of the surface material with at least one sensor; and
   relating said electrical property to the article condition.

2. The method as claimed in claim 1 wherein processing comprises shot peening.

3. The method as claimed in claim 1 wherein processing comprises laser welding.

4. The method as claimed in claim 1 wherein the condition is stress.

5. The method as claimed in claim 1 wherein the condition is temperature.

6. The method as claimed in claim 1 wherein the sensor is an eddy current sensor.

7. The method as claimed in claim 1 wherein the sensor is an eddy current sensor array.

8. The method as claimed in claim 7 further comprising: mounting the sensor array to the article surface.

9. The method as claimed in claim 7 further comprising: scanning the sensor array over the article surface.

10. The method as claimed in claim 1 wherein the electrical property is magnetic permeability.

11. The method as claimed in claim 1 wherein the electrical property is electrical conductivity.

12. The method as claimed in claim 1 wherein the condition is mechanical overload.

13. The method as claimed in claim 1 wherein the condition is thermal overload.

* * * * *